United States Patent [19]
Zinnanti et al.

[11] Patent Number: 5,135,526
[45] Date of Patent: Aug. 4, 1992

[54] ELECTRO-CAUTERY SPECULUM

[75] Inventors: William J. Zinnanti, Chatsworth; Anthony Zinnanti, Jr., Bell Canyon, both of Calif.

[73] Assignee: Zinnanti Surgical Instruments, Inc., Chatsworth, Calif.

[21] Appl. No.: 688,434

[22] Filed: Apr. 22, 1991

[51] Int. Cl.⁵ ............................................... A61B 1/12
[52] U.S. Cl. ........................................... 606/49; 128/3
[58] Field of Search ................ 606/49, 127, 128, 159; 128/3; 604/902, 164, 171, 264

[56] References Cited

U.S. PATENT DOCUMENTS

| | | | |
|---|---|---|---|
| 3,132,645 | 5/1964 | Gasper | 128/3 |
| 4,633,865 | 1/1987 | Hengstberger et al. | 128/3 X |
| 4,683,884 | 8/1987 | Hatfield et al. | 606/49 |
| 4,719,914 | 1/1988 | Johnson | 606/49 X |

FOREIGN PATENT DOCUMENTS

| | | | |
|---|---|---|---|
| 78668 | 9/1917 | Austria | 128/3 |
| 252391 | 1/1912 | Fed. Rep. of Germany | 128/3 |

Primary Examiner—Peter A. Aschenbrenner
Attorney, Agent, or Firm—Allen A. Dicke, Jr.

[57] ABSTRACT

Redundant wall retractor is tubular and is obturated for insertion. It has a duct which terminates in an opening at the top of the anterior end and terminates with a tube fitting at the bottom at the posterior end. It is made of dielectric synthetic polymer composition material, preferably transparent to retract tissues during loop electrode excision procedures with the duct positioned for withdrawing smoke.

20 Claims, 1 Drawing Sheet

U.S. Patent     Aug. 4, 1992     5,135,526
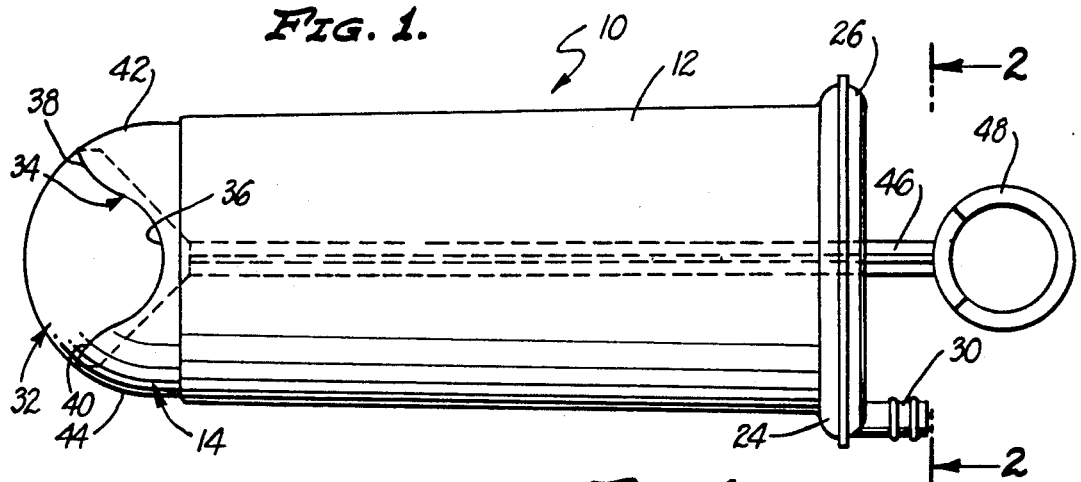
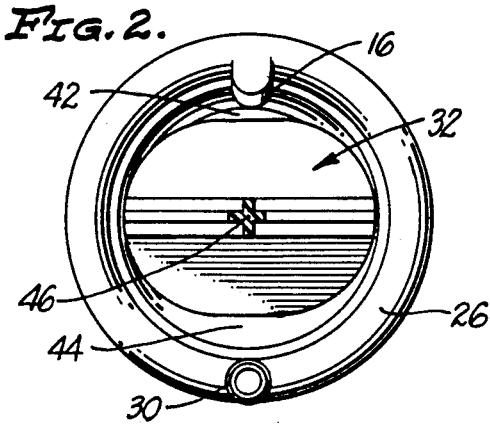
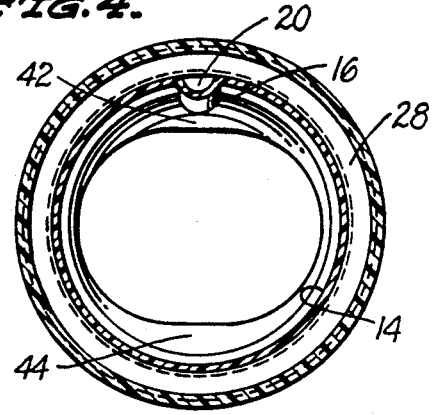
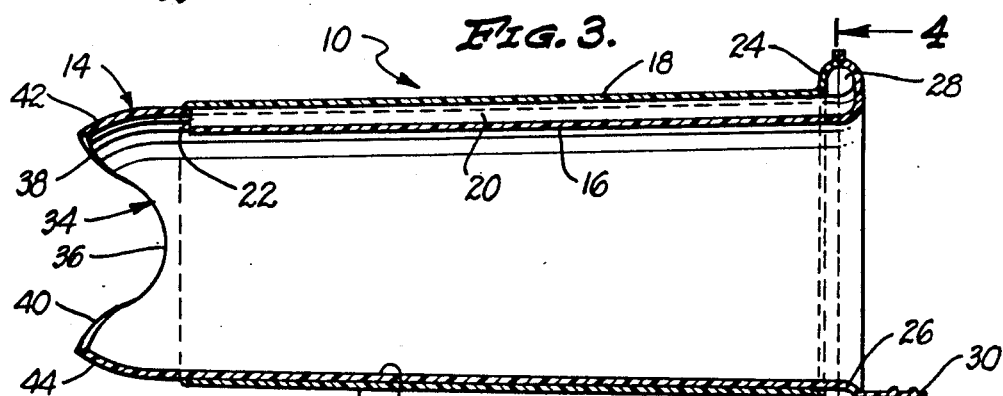
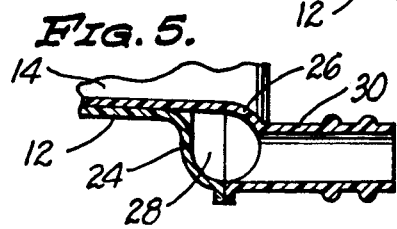
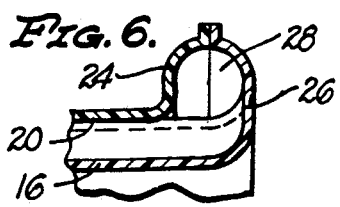

ELECTRO-CAUTERY SPECULUM

FIELD OF THE INVENTION

This invention is directed to an electro-cautery speculum particularly useful in loop electrode excision procedures wherein the speculum is dielectric and a smoke-withdrawal duct is positioned at the anterior end to aid in maintaining a clear field.

BACKGROUND OF HE INVENTION

Electro-cautery presents a set of problems which are not satisfied with any present speculum. Loop electrode excision procedures employ an electrode at a significant voltage. Thus, the present metallic speculums are unsatisfactory because of the chance of the loop touching and charging the metallic speculum. This problem is exacerbated by the employment of a redundant wall speculum to maximize the field, but the present-day redundant wall speculums are also metallic. In addition, in loop electrode excision procedures, smoke is created, but a smoke-withdrawal tube is not placed in the optimum position. The use of a separate smoke-withdrawal tube obstructs the field. Thus, there is need for an electro-cautery speculum which provides safety and which improves vision of and access to the field.

SUMMARY OF THE INVENTION

In order to aid in the understanding of this invention, it can be stated in essentially summary form that it is directed to an electro-cautery speculum which is substantially a right circular cylindrical tube of dielectric thermoplastic material and which is preferably transparent. The speculum has an obturator for closing the anterior end during insertion and is, thereupon, removed through the posterior end. A duct is provided at an optimum location at the anterior end to withdraw smoke from the speculum.

It is, thus, an object and advantage of this invention to provide a dielectric electro-cautery speculum which renders the patient safe from electrical shock which would be caused by loop electrode contact with a metallic speculum.

It is another object and advantage of this invention to provide an electro-cautery speculum which places a smoke-withdrawal duct inlet at the optimum location a the anterior of the speculum so as to withdraw smoke to maximize clarity of vision at the field.

It is another object and advantage of this invention to provide an electro-cautery speculum which is tubular in form and which has a removable obturator so that the speculum can be comfortably inserted and the obturator then withdrawn from the posterior end to provide access to the field.

It is another object and advantage of this invention to provide an electro-cautery speculum which is inexpensively manufactured of synthetic polymer composition materials so that the speculum can be economically provided and disposed of after a single use.

Other objects and advantages of this invention will become apparent from a study of the following portion of the specification, the claims and the attached drawings.

BRIEF DESCRIPTION OF THE DRAWINGS

FIG. 1 is a side-elevational view of the electro-cautery speculum of this invention.

FIG. 2 is an end-elevational view, as seen generally along 2—2 of FIG. 1.

FIG. 3 is a center-line longitudinal section through the speculum of FIG. 1, with the obturator removed.

FIG. 4 is a section taken generally along 4—4 of FIG. 3.

FIG. 5 is an enlarged longitudinal section, with parts broken away, of the lower posterior corner.

FIG. 6 is an enlarged longitudinal section, with parts broken away, of the upper posterior corner of the speculum.

DESCRIPTION OF THE PREFERRED EMBODIMENT

The electro-cautery speculum of this invention is generally indicated at 10 in FIGS. 1 and 3. The purpose of the speculum is to retract the vaginal walls to allow access to the cervix for electro-cautery thereof. A duct for withdrawal of smoke resulting from the electro-cautery procedure is placed at an optimum location. The speculum 10 has two body parts, as is best seen in FIG. 3. The outer tube 12 and inner tube 14 are thin-walled generally conical tubes with enough cone to provide the draft helpful in the injection-molding process. Except for this molding draft and the duct built into the tubes 12 and 14, they could be right circular cylindrical tubes.

As is seen in FIGS. 3 and 4, inner tube 14 has a duct wall 16 which is substantially in the form of a hemicylindrical tube in that portion of the wall. Similarly, outer tube 12 preferably may have a companion ridge 18 extending radially outward in the outer tube and extending the length thereof so that the duct wall 16 and ridge 18 form a duct 20 throughout the length of inner tube 14. The anterior end of duct 20 forms duct opening 22. At the posterior end, a one-quarter annular duct ring 24 is formed on outer tube 12. A companion three-quarter annular duct ring 26 is provided on the posterior end of inner tube 14. It is understood that the inner and outer tubes are each a one-piece injection molding. When they are fitted together, as shown in FIG. 3, it is seen that the duct 20 is formed and the annular duct 28 is also formed, with the ducts joined together. The joints are sealed by adhesive or other joining methods, such as ultrasonic welding. Tube fitting 30 forms a part of duct ring 26. It is significant to note that the tube fitting 30 is diametrically opposite the duct opening 22. This positioning is so that the duct opening 22 can be positioned above the site of the procedure and the tube fitting 30 is below the opening into the posterior end of tube 14. FIGS. 5 and 6 show the details by which the annular duct 28 is formed and is connected to the duct 20 and tube fitting 30.

In order to provide for comfortable insertion, the speculum is obturated during insertion Obturator 32 fills the anterior opening of the speculum during insertion. Obturator 32, together with the anterior end of inner tube 14, forms a hemispherical dome, as seen in FIG. 1. The dividing line between the obturator 32 and the anterior end of tube 14 is of double curve configuration, as seen in FIG. 1. The anterior end 34 of the tube 14 has a substantially half-cylindrical concave wall 36 and substantially quarter-circular cylindrical convex walls 38 and 40. This configuration leaves an upper flange 42 and a lower flange 44. The walls 36, 38 and 40 on the flanges are substantially parallel to the axial center line, left to right through FIGS. 1 and 3 and perpendicular to the sheet at the center of FIGS. 2 and 4. The dome of the obturator 32 completes the hemispherical shape of the anterior end, and the obturator has corresponding walls which lie against the walls 36, 38 and 40. The obturator 32 lies against the inside of the flanges 42 and 44 to define a forward limit for the obturator. In addition, the obturator carries a stem 46 which has thereon ring 48. The ring 48 is engaged with the thumb, while the index and middle fingers grasp the anterior side of the duct ring to hold the obturator in place and guide the speculum during insertion.

At completion of insertion, the obturator is withdrawn by grasp on the ring 48 and withdrawal of the obturator in the posterior direction. A vacuum tube is connected onto fitting 30. The speculum is then in place for electro-cautery procedures. A sufficient opening is provided at the anterior end for an adequate surgical field. Smoke is withdrawn at the top of the field to maximize visibility during the procedure. The tube on fitting 30 drapes away without obstructing the field. The electro-cautery speculum 10 is preferably made of injection-moldable thermoplastic synthetic polymer composition material of dielectric nature to prevent electric shock problems. Furthermore, it is preferably made of a transparent polymer so that adjacent tissues may also be observed. The speculum 10 can be manufactured in a sufficiently inexpensive manner that it can be disposed of after a single use. It can be supplied in sterile packaging and disposed of after the single use to avoid contamination.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An electro-cautery speculum comprising:
   a tube, said tube having an anterior end and a posterior end, said tube also having a top and a substantially opposite bottom;
   a duct mounted on said tube, said duct having an inlet opening on the interior of said tube at the top thereof adjacent said anterior end and having an outlet adjacent the posterior end of said tube at the bottom thereof; and
   a removable obturator at the anterior end of said tube, said removable obturator being removable through said tube and at said posterior end of said tube.

2. The electro-cautery speculum of claim 1 wherein said speculum is made of dielectric material.

3. The electro-cautery speculum of claim 2 wherein said material is transparent synthetic polymer composition material.

4. The electro-cautery speculum of claim 1 wherein the anterior end of said speculum and said obturator combine to make a substantially hemispherical anterior surface on said speculum to aid in insertion.

5. The electro-cautery speculum of claim 4 wherein said speculum has flanges thereon, said flanges having surfaces substantially parallel to the length of said speculum between said anterior and posterior ends, said obturator being engaged against said flanges when in place.

6. The electro-cautery speculum of claim 5 wherein said obturator has a stem thereon, said stem being sized so that when said obturator is in obturating position, said stem extends sufficiently toward said posterior end of said speculum to be graspable for withdrawal from between said flanges and out through said posterior end.

7. The electro-cautery speculum of claim 6 wherein said speculum is made of dielectric material.

8. The electro-cautery speculum of claim 7 wherein said material is transparent synthetic polymer composition material.

9. The electro-cautery speculum of claim 1 wherein said duct is formed as part of said speculum.

10. The electro-cautery speculum of claim 9 wherein at least a portion of said speculum is formed of inner and outer tubes, said inner and outer tubes having walls therein which define said duct.

11. The electro-cautery speculum of claim 10 wherein said duct includes a duct ring extending at least a portion of the way around the posterior end of said speculum.

12. An electro-cautery speculum comprising:
    an inner tube, said inner tube having a posterior end and an anterior end, said inner tube having an opening therethrough from said posterior end to said anterior end, said inner tube having an axis extending from end to end and having a top side and a bottom side;
    walls at least partially in said inner tube defining a duct extending from adjacent said top at said anterior end to adjacent said bottom at said posterior end; and
    an obturator positioned within said anterior opening and removable through said inner tube out of said posterior end so that said speculum can be positioned with its obturator in place and the obturator can thereupon be removed for electro-cautery procedures.

13. The electro-cautery speculum of claim 12 wherein said speculum is made of dielectric materials.

14. The electro-cautery speculum of claim 13 wherein said speculum is made of dielectric clear thermoplastic synthetic polymer composition material for single use.

15. The electro-cautery speculum of claim 12 further including an outer tube, said outer tube engaging said inner tube where said walls define said duct to close said duct walls to form said duct.

16. The electro-cautery speculum of claim 15 wherein said walls include an annular duct at said posterior end of said speculum, said annular duct being in communication with said duct opening adjacent said anterior end of said speculum.

17. The electro-cautery speculum of claim 16 further including a tube fitting attached to said annular duct so that vacuum can be drawn on said tube fitting and on said duct to withdraw gas from said anterior end of said speculum.

18. The method of forming and using an electro-cautery speculum comprising the steps of:
    forming a tubular speculum of dielectric transparent material with a smoke duct extending from its anterior to its posterior end;
    inserting the speculum with an obturator in place;
    withdrawing the obturator through the speculum;
    withdrawing gas from the upper anterior portion of the speculum out through the lower posterior portion of the speculum to aid in maintaining a clear visible field; and
    performing electro-cautery adjacent the anterior end of the speculum.

19. The method of claim 18 wherein the fabricating step comprises molding the speculum and the obturator of dielectric transparent thermoplastic synthetic polymer composition material.

20. The method of claim 19 further including inspecting through the transparent walls of the speculum.

* * * * *